United States Patent [19]

Kolasa et al.

[11] Patent Number: 5,691,351
[45] Date of Patent: Nov. 25, 1997

[54] BIS-(HETEROARYLMETHOXYPHENYL) CYCLOALKYL CARBOXYLATES AS INHIBITORS OF LEUKOTRIENE BIOSYNTHESIS

[75] Inventors: Teodozyj Kolasa, Lake Villa; David E. Gunn, Waukegan; Clint D. W. Brooks, Libertyville, all of Ill.

[73] Assignee: Abbott Laboratories, Abbott Park, Ill.

[21] Appl. No.: 596,058

[22] Filed: Feb. 6, 1996

[51] Int. Cl.$^6$ .......................... A61K 31/47; C07D 401/12
[52] U.S. Cl. .......................... 514/314; 514/249; 514/367; 544/353; 546/152; 546/174; 548/156
[58] Field of Search .......................... 514/314, 249, 514/367; 544/353; 546/152, 174; 548/156

[56] References Cited

PUBLICATIONS

Cope, et al., cis,cis–1,5–Cyclooctadiene Diepoxide, The Journal of Organic Chemistry, vol. 84, No. 7, Jul., (1989), pp. 2231–2234.

von Leander Tenud, et al., 1,3–Cyclobutandionderivate aus Keten, Helvetica Chimica Acta, vol. 60, Fasc. 3,, (1977)—Nr. 100, pp. 975–977.

McIntosh, J. M., An Improved Preparation of 1,3–Cyclopentanedione, J. Org. Chem, vol. 37. No. 18, (1972), pp. 2905–2906.

Dowd, P., et al., Novel Free Radical Ring–Expansion Reaction, Tetrahedron, vol. 45, No.1, (1989), pp. 77–90.

Bashir–Hashemi, A., et al., Regioselectivity in Photochemical Chlorocarbonylation of Carbonyl Compounds, J. Org. Chem, vol. 59, No. 8, 1994, pp. 2132–2134.

Curran, D. P., et al., Tandem Transannular Radical Cyclizations. Total Synthesis of (+/–)–Modhephene and (+/–)–Epi––Modhephane, Tetrahedron, vol. 49, No. 4, 1993, pp. 755–770.

Miur, H., et al., Synthese von 5–substituierten Cyclooctynen, Communications, Aug., 1978, pp.596–598.

Primary Examiner—Jacqueline Haley
Attorney, Agent, or Firm—Monte R. Browder

[57] ABSTRACT

Compounds having the structure

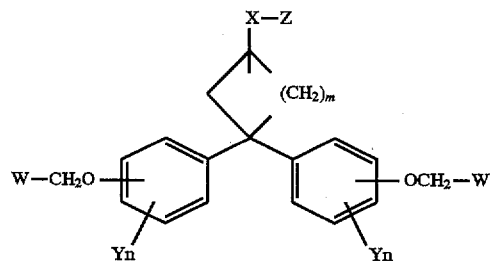

where m is an integer of from one to nine; n is an integer of from one to four; W is selected from substituted or unsubstituted quinolyl, benzothiazolyl, or quinoxalyl, X is selected from $C_{1-6}$ alkylene, $C_{2-6}$ alkenylene and $C_{2-6}$ alkynylene; Y is selected from halogen, $C_{1-6}$ alkyl and $C_{1-6}$ alkoxy; and Z is selected from —C(O)B; —C(R$_2$)$^2$—O—N=A—C(O)B; and —C(R$^2$)=N—O—A—C(O)B where A is $C_{1-6}$ alkylene and B is —OH, —O—M$^+$, —OD where D is a metabolically cleavable group, —OR$^6$ where R$^6$ is hydrogen or $C_{1-6}$ alkyl, —NR$^6$R$^7$ where R$^7$ is hydrogen, $C_{1-6}$ alkyl, hydroxy or $C_{1-6}$ alkoxy, or where R$^6$ and R$^7$ taken together form a five to eight membered ring optionally containing one heteroatom selected from nitrogen, oxygen or sulfur, are inhibitors of leukotriene biosynthesis.

8 Claims, No Drawings

BIS-(HETEROARYLMETHOXYPHENYL) CYCLOALKYL CARBOXYLATES AS INHIBITORS OF LEUKOTRIENE BIOSYNTHESIS

TECHNICAL FIELD

The present invention relates to novel compounds having activity to inhibit leukotriene effects, to pharmaceutical compositions comprising these compounds, and to a medical method of treatment. More particularly, the present invention concerns symmetrical bis-heteroarylmethoxyphenylcycloalkyl compounds which inhibit leukotriene effects, to pharmaceutical compositions comprising these compounds and to a method of inhibiting leukotriene biosynthesis.

BACKGROUND OF THE INVENTION

The leukotrienes are extremely potent substances which produce a wide variety of biological effects, often in the nanomolar to picomolar concentration range. Leukotrienes are important pathological mediators in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

Compounds which prevent leukotriene biosynthesis are thus useful in the treatment of disease states such as those listed above in which the leukotrienes play an important pathophysiological role.

U.S. Pat. No. 4,970,215 to Mohrs et al. discloses and claims certain 4-(quinolin-2-ylmethoxy)phenyl cycloalkyl acetic acids as inhibitors of leukotriene biosynthesis.

European Patent Application 0 349 062 to Zamboni et al. discloses and claims certain 2-quinolylmethoxyphenyl substituted thioalkanoic acid derivatives as leukotriene biosynthesis inhibitors. Prasit et al. in *Bioorganic and Medicinal Chemistry Letters*, 1: 645–648 (1991) describe {[4-(4-chlorophenyl)-1-[4-(2-quinolylmethoxy)phenyl]-butyl]thio}acetic acid, L-674,636, as a new, potent and orally active leukotriene synthesis inhibitor.

U.S. Pat. No. 5,358,955 to Brooks et al. discloses and claims certain quinolylmethoxyphenyl derivatives as inhibitors of leukotriene biosynthesis.

SUMMARY OF THE INVENTION

In its principal embodiment, the present invention provides certain symmetrical bis-heteroarylmethoxyphenylcycloalkyl carboxylate compounds and pharmaceutically acceptable salts thereof having the formula I:

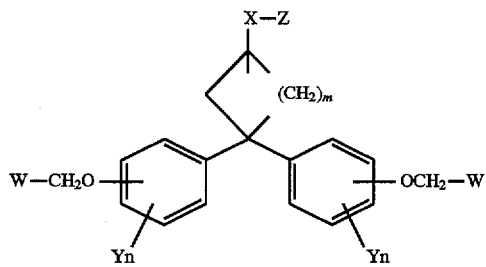

In the compound of formula I above, m is an integer of 1 to 9, inclusive and n is an integer of 1 to 4, inclusive The group W is the same at each occurrence and is selected from the group consisting of (a) unsubstituted quinolyl; (b) quinolyl substituted with one, two, or three susbstituents selected from the group consisting of halogen, $C_{1-6}$ alkyl, and $C_{1-6}$ alkoxy; (c) unsubstituted benzothiazoyl; (d) benzothiazoyl substituted with one, two, or three susbstituents selected from the group consisting of halogen, $C_{1-6}$ alkyl, and $C_{1-6}$ alkoxy; (e) unsubstituted quinoxalyl; and (f) quinoxalyl substituted with one, two, or three susbstituents selected from the group consisting of halogen, $C_{1-6}$ alkyl, and $C_{1-6}$ alkoxy.

The group Y is one to four optional substituents selected from: halogen, $C_{1-6}$ alkyl, and $C_{1-6}$ alkoxy;

X is absent or is selected from the group consisting of (a) $C_{1-6}$ alkylene; (b) $C_{1-6}$ alkenylene; and (c) $C_{1-6}$ alkynylene.

Z is selected from the group consisting of (a) COB; (b) $C(R^2)_2$—O—N=A—COB; and (c) $C(R^2)$=N—O—A—COB where A is $C_{1-6}$ alkylene, and B is selected from the group consisting of (a) —OH, (b) —O—$M^+$ where M is a pharmaceutically acceptable cation; (c) —$OR^6$ where $R^6$ is hydrogen or alkyl of one to six carbon atoms; (d) —$NR^6R^7$ where $R^6$ is as previously defined and $R^7$ is selected from the group consisting of hydrogen, alkyl of one to six carbon atoms, hydroxy, and alkoxy or from one to six carbon atoms, or $R^6$ and $R^7$, together with the atom to which they are attached, form a ring of five to eight members containing one optional heteroatom selected from N, O and S; and (e) —O—D where D is a metabolically cleavable group.

The present invention also provides pharmaceutical compositions which comprise a leukotriene biosynthesis inhibitory effective amount of compound as defined above in combination with a pharmaceutically acceptable carrier.

The invention further relates to a method of inhibiting leukotriene biosynthesis in a host mammal in need of such treatment comprising administering to a mammal in need of such treatment a therapeutically effective amount of a compound as defined above.

DETAILED DESCRIPTION

As used throughout this specification and the appended claims, the following terms have the meanings specified.

The term alkyl refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms alkoxy and alkoxyl denote an alkyl group, as defined above, attached to the parent molecular moiety through an oxygen atom. Representative alkoxy groups include methoxy, ethoxy, propoxy, butoxy, and the like.

The terms alkenyl as used herein refer to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term alkylene denotes a divalent group derived from a straight or branched chain saturated hydrocarbon containing by the removal of two hydrogen atoms, for example —$CH_2$—, —$CH_2CH_2$—, —$CH(CH_3)CH_2$— and the like.

The term alkenylene denotes a divalent group derived from a straight or branched chain hydrocarbon containing at least one carbon-carbon double bond. Examples of alkenylene include —CH=CH—, —$CH_2$CH=CH—, —$C(CH_3)$=CH—, —$CH_2$CH=$CHCH_2$—, and the like.

The terms alkynylene refers to a divalent group derived by the removal of two hydrogen atoms from a straight or branched chain acyclic hydrocarbon group containing at least one carbon-carbon triple bond. Examples of alkynylene include —C≡CH—, —C≡C—$CH_2$—, —C≡CH—$CH(CH_3)$— and the like.

The term aryl as used herein refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like.

The term cycloalkyl as used herein refer to a monovalent saturated cyclic hydrocarbon group. Representative cycloalkyl groups include cyclopropyl, cyclobutyl, cyclopentyl, cyclohexyl, cycloheptyl, bicyclo[2.2.1]heptane and the like.

Cycloalkylene denotes a divalent radical derived from a cycloalkane by the removal of two hydrogen atoms.

The term haloalkyl denotes an alkyl group, as defined above, having one, two, or three halogen atoms attached thereto and is exemplified by such groups as chloromethyl, bromoethyl, trifluoromethyl, and the like.

The term metabolically clearable group denotes a group which is cleaved in vivo to yield the parent molecule of the formula I indicated above wherein M is hydrogen. Examples of metabolically cleavable groups include —COR, —COOR, —CONRR and —$CH_2$OR radicals where R is selected independently at each occurrence from alkyl, trialkylsilyl, carbocyclic aryl or carbocyclic aryl substituted with one or more of $C_1$–$C_4$ alkyl, halogen, hydroxy or $C_1$–$C_4$ alkoxy. Specific examples of representative metabolically cleavable groups include acetyl, methoxycarbonyl, benzoyl, methoxymethyl and trimethylsilyl groups.

The terms phenylene, pyridylene, thienylene, and furylene refer to divalent radicals derived by the removal of two hydrogen atoms from the ring systems of benzene, pyridine, thiophene, and furan, respectively.

By pharmaceutically acceptable salt it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, titrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like.

Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts In one preferred embodiment of the present invention, compounds of the present invention have the generic structure I indicated above wherein W is unsubstituted quinolyl or quinolyl substituted with one, two, or three susbstituents selected from the group consisting of halogen, $C_{1-6}$ alkyl, and $C_{1-6}$ alkoxy.

In another preferred embodiment, compounds of the present invention have the generic structure I indicated above wherein W is unsubstituted benzothiazolyl or benzothiazolyl substituted with one, two, or three susbstituents selected from the group consisting of halogen, $C_{1-6}$ alkyl, and $C_{1-6}$ alkoxy.

In yet another preferred embodiment, compounds of the present invention have the generic structure I indicated above wherein W is unsubstituted quinoxalyl or quinoxalyl substituted with one, two, or three substituents selected from the group consisting of halogen, $C_{1-6}$ alkyl, and $C_{1-6}$ alkoxy.

In a particularly preferred embodiment of the present invention, W is unsubstituted or substituted quinolyl, m is an integer of from 1 to three, inclusive, and X is methylene.

Examples of compounds falling within the scope of the present invention include, but are not limited to:

4,4-bis-(4-(2-quinolylmethoxy)phenyl)cyclohexane carboxylic acid;

4,4-bis-(4-(2-quinolylmethoxy)phenyl)cyclohexane carboxylic acid sodium salt;

4,4-bis-(4-(2-quinolylmethoxy)phenyl) cyclohexyliminoxyacetic acid sodium salt;

4,4-bis-(4-(2-quinolylmethoxy)phenyl) cyclohexyliminoxy-2-propionic acid sodium salt;

4,4-bis-(4-(2-quinolylmethoxy)phenyl)-1-cyclohexylmethyliminoxyacetic acid; and 4,4-bis-(4-(2-quinolylmethoxy)phenyl)-1-cyclohexyloximinoacetic acid Lipoxygenase Inhibition Determination Leukotriene biosynthesis inhibitory activity of representative compounds of the present invention was evaluated in an assay involving calcium ionophore-induced $LTB_4$ expressed in human polymorphornuclear leukocytes (PMNL). Human PMNL isolated from heparinized (20 USP units/mL) venous blood (25 mL) obtained from healthy volunteers was layered over an equal volume of Ficoll-Hypaque Mono-Poly Resolving Medium (ICN Flow, Costa Mesa, Calif.) and centrifugated at 400×g for 40 min at 20° C. The PMNL was collected, erythrocytes lysed and washed 2× and suspended at $1.0 \times 10^7$ cells/mL in Earle's balanced salt solution with 17 mM Earle's HEPES. Aliquots of the cell suspension were preincubated with test compounds dissolved in DMSO (final concentration <2%) for 15 min. and stimulated with calcium ionophore (final concentration 8.3 µM) for 10 min. at 37° C. Incubations were stopped with the addition of two volumes of ice-cold methanol followed by centrifuging the cell suspensions at 4° C. for 10 min at 450×g. The mount of $LTB_4$ in the methanol extract was analyzed by enzyme-linked immunoassay or by HPLC analysis.

The compounds of this invention inhibit leukotriene biosynthesis as shown by the data for representative examples in Table 1.

TABLE 1

Inhibitory Potencies Against Calcium Ionophore Stimulated
Leukotriene Formation in Human Polymorphonuclear Leukocytes

| Example | $IC_{50}$ (nM) |
|---------|----------------|
| 1 | 59 |
| 2 | 47 |
| 5 | 37 |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuseular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coating well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The commercially available, ethyl 4-oxocyclohexanecarboxylate I is reacted with phenol in the presence of a cone. $H_2SO_4$ to provide adduct II. Adduct II is convened to the corresponding bis-quinoline derivative III by treatment with heteroarylmethylhalide (W—$CH_2$X where X is Cl, Br, or I) in the presence of a suitable base such as $K_2CO_3$. The bis-quinoline intermediate III is hydrolyzed with hydroxide to provide the compounds of this invention represented by IV.

The compound IV can be reduced to alcohol V using standard methods and then transformed into additional compounds of this invention, the iminoxy alkylcarboxylate VI by applying methods outlined in Scheme 2.

1,4-Cyclohexanedione moncethylene ketal I is reduced by known methods such as with $NaBH_4$ to provide the corresponding hydroxy intermediate II. The hydroxy intermediate II is reacted with phenol in the presence of conc. $H_2SO_4$ to provide diphenol derivative III. The diphenol derivative III is then reacted with the requisite heteroarylmethylhalide (W—$CH_2$X) in the presence of a suitable base as $K_2CO_3$ to afford adduct IV. The adduct IV is converted to the corresponding hydroxylamine derivative by known methods such as the Mitsunobu reaction with N-hydroxyphthalimide as nucleophile to provide the intermediate V which is converted to the correspoding O-alkylhydroxylamine VI by the known method or treatment with hydrazine hydrate. The O-alkylhydroxylamine derivative VI is then reacted in a standard manner with the requisite carbonyl unit, O=CR—A—COB to provide the compounds of this invention represented by the general structure VII.

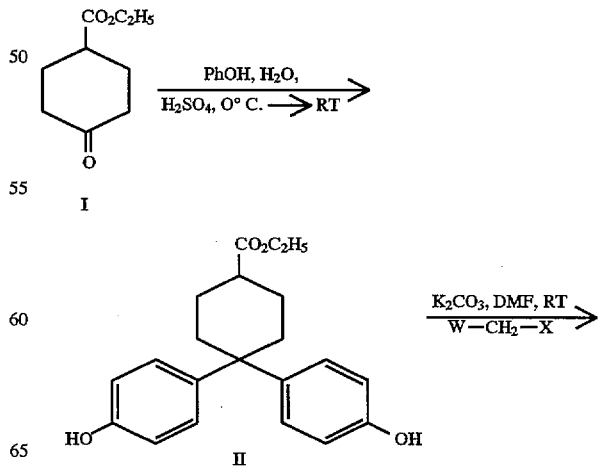

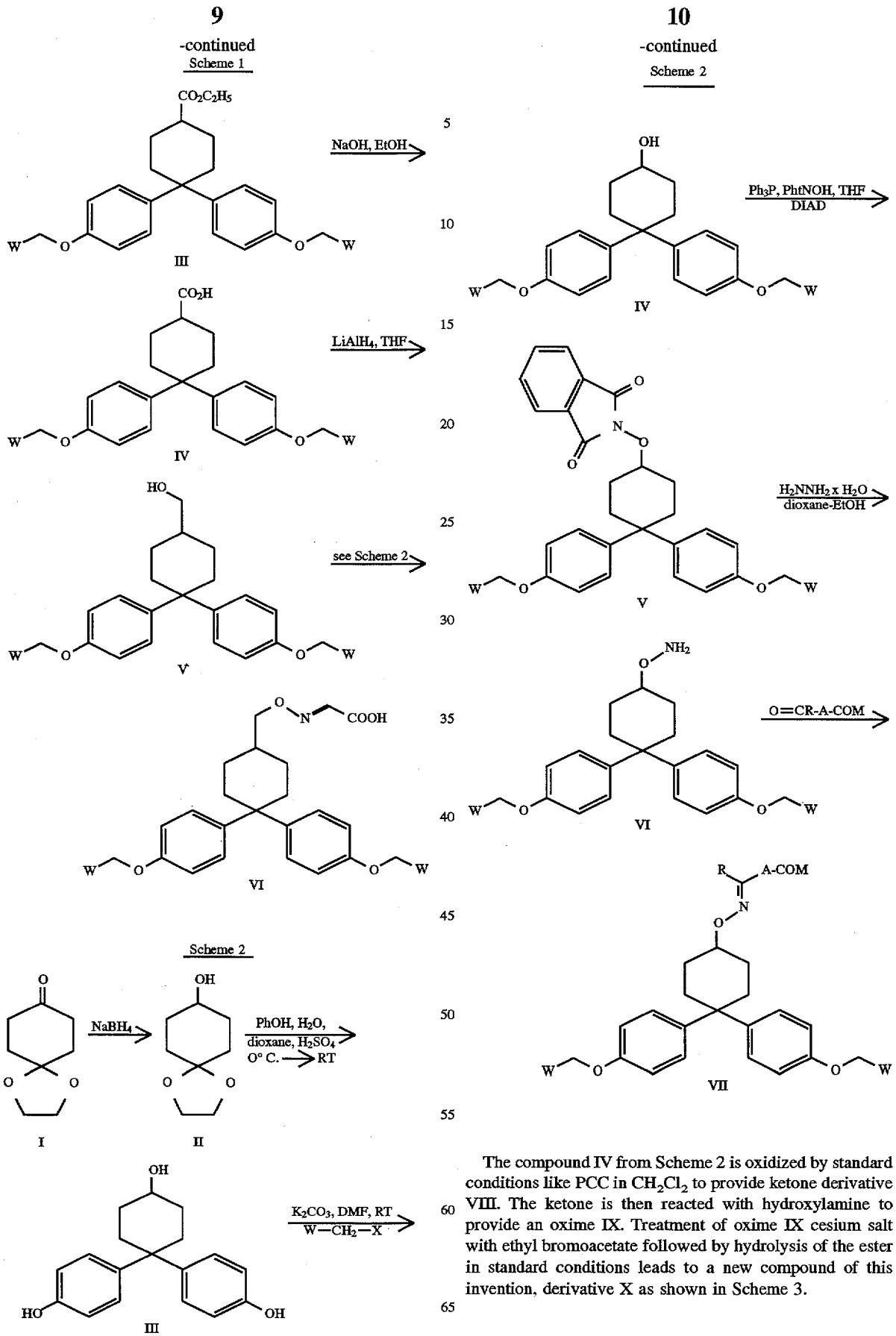

The compound IV from Scheme 2 is oxidized by standard conditions like PCC in $CH_2Cl_2$ to provide ketone derivative VIII. The ketone is then reacted with hydroxylamine to provide an oxime IX. Treatment of oxime IX cesium salt with ethyl bromoacetate followed by hydrolysis of the ester in standard conditions leads to a new compound of this invention, derivative X as shown in Scheme 3.

Scheme 3

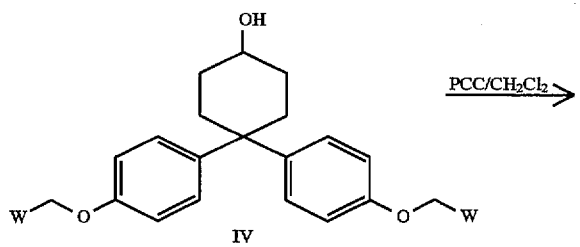

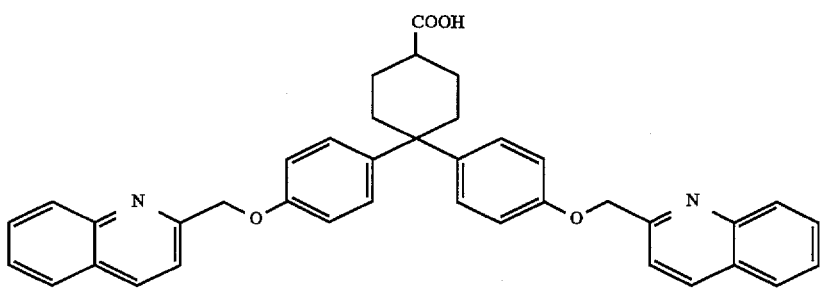

-continued
Scheme 3

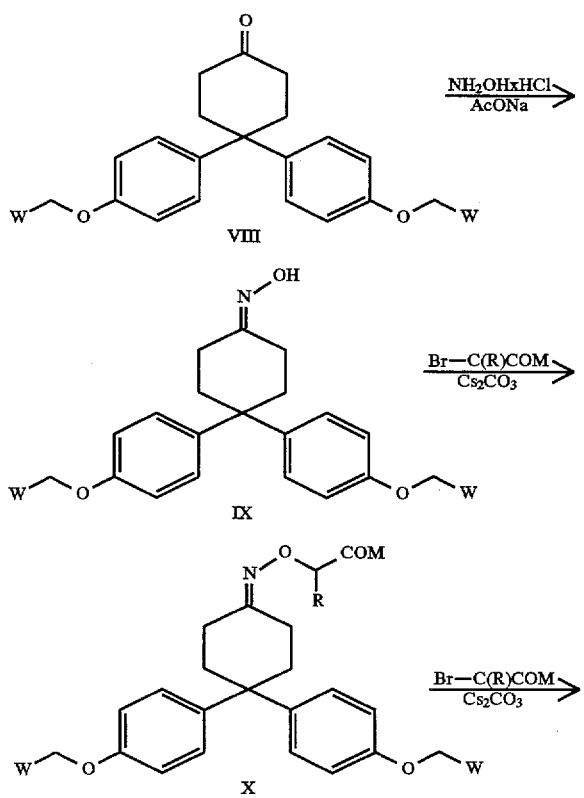

The foregoing may be better understood by reference to the following examples which are provided for illustration and not intended to limit the scope of the invention as it is defined by the appended claims.

EXAMPLE 1

Preparation of 4,4-bis-(4(2-quinolylmethoxy)phenyl)cyclohexane carboxylic acid

Phenol (1.1 g, 11.8 mmol) was diluted with water (0.53 mL) and cooled to 0° C. with stirring. Ethyl 4-oxocyclohexanecarboxylate (0.94 mL, 5.87 mmol) was added followed by dropwise addition of concentrated $H_2SO_4$ (2.11 g). After 10 min the mixture was warmed to room temperature and allowed to stir for 4 hr. The mixture was then diluted with water and the product extracted with EtOAc (2×). The organic layer was washed with water, brine, dried over $MgSO_4$ and concentrated in vacuo. The residue was purified by chromatography (silica gel, 2:1 Hexane/EtOAc) to give 1.01 g (51%) of 4,4-bis(4-hydroxyphenyl)cyclohexane carboxylic acid ethyl ester.

To a solution of intermediate diphenol (0.93 g, 2.73 mmol) and $K_2CO_3$ (1.04 g, 7.52 mmol) in DMF (50 mL) at room temperature was added 2-chloromethylquinoline hydrochloride (0.97 g, 5.27 mmol) and the mixture was allowed to stir for 24 hr. The mixture was diluted with water and the product extracted with EtOAc (2×). The organic layer was washed with water, brine, dried over $MgSO_4$ and concentrated in vacuo. The residue was triturated with hexanes and the precipitating solid was filtered and washed with hexanes to give 1.30 g (77%) of 4,4-bis(4-(2-quinolylmethoxy)phenylcyclohexanecarboxylic acid ethyl ester as a white powder.

The ester (0.52 g, 0.84 mmol) was suspended in EtOH at room temperature and 1N NaOH (1.01 mL, 1.01 mmol) was added to the solution. The resulting mixture was refluxed for 6 hr. The reaction mixture was then cooled and diluted with water. The EtOH was removed in vacuo. and the resulting aqueous solution was acidified with 10% citric acid to pH 3. The solid was filtered under vacuum and washed with water followed by hexanes to give 0.50 g (99%) of the title compound as a white powder: mp 194°–199° C.; $^1H$ NMR (300 MHz, DMSO-$d_6$) δ 1.45 (m, 2H), 1.76 (m, 2H), 1.88 (m, 2H), 2.33 (m, 1H), 2.62 (m, 2H), 5.31 (d, J=10.50 Hz, 4H), 6.90 (d, J=9 Hz, 2H), 7.00 (d, J=9 Hz, 2H), 7.13 (d, J=9 Hz, 2H), 7.28 (d, J=9 Hz, 2H, 7.62 (m, 3H), 7.68 (d, J=9 Hz, 1H), 7.78 (m, 2H), 8.00 (m, 4H), 8.40 (t, J=7.50 Hz, 2H), 12.04 (br s, 1H); MS (DCI-NH$_3$) m/z 595 (M+H)$^+$; Anal. Calcd for C$_{39}$H$_{34}$N$_2$O$_4$.0.70 H$_2$O: C, 77.13; H, 5.87; N, 4.61; Found: C, 77.20; H, 5.84; N, 4.45.

EXAMPLE 2

Preparation of 4,4-bis-(4-(2-quinolylmethoxy) phenyl)cyclohexane carboxylic acid sodium salt To the acid (0.62 g, 1.05 mmol), as prepared in Example 1, in THF (10 mL) was added 1N NaOH (1.0 mL, 1.0 mmol) was added and the mixture was allowed to stir for 2 hr at room temperature. The organic solvent was removed in vacuo and the residue was triturated with Et$_2$O and filtered under vacuum. The solid was washed many times with Et$_2$O to remove the remaining carboxylic acid to give 0.60 g (93%) of the title compound as a white powder. $^1$H NMR (300 MHz, DMSO-d$_6$) δ 1.43 (m, 2H), 1.63 (m, 2H), 1.80 (m, 4H), 2.56 (m, 1H), 5.29 (d, J=9 Hz, 4H), 6.89 (d, J=9 Hz ,2H), 6.97 (d, J=9 Hz, 2H), 7.12 (d, J=9 Hz, 2H), 7.25 (d, J=9 Hz, 2H), 7.61 (m, 2H), 7.67 (d, J=9 Hz, 2H), 7.78 (m, 2H), 8.00 (m, 4H), 8.39 (dd, J=9, 6 Hz, 2H); MS (DCI-NH$_3$) m/z 617 (M+Na)$^+$, 639 (M+2Na–H)$^+$; Anal. Calcd for C$_{39}$H$_{33}$N$_2$O$_4$Na.1.30H$_2$O: C, 73.18; H, 5.60; N, 4.38; Found: C, 73.23; H, 5.33; N, 4.25.

EXAMPLE 3

Preparation of 4,4-bis-(4(2-quinolylmethoxy) phenyl)-1-cyclohexymethanol filtered and concentrated in vacuo. The residue was purified by chromatography (silica gel, 1:1Hexane/EtOAc) to give 250 mg of the title compound as a white powder: mp 61°–68° C.; $^1$H NMR (300MHz, DMSO-d$_6$) δ 0.99 (m, 2H), 1.47 (m, 1H), 1.63 (m, 2H), 1.76 (m, 2H), 2.67 (m, 2H), 3.11 (m, 2H), 4.31 (m, 1H), 5.28 (s, 2H), 5.32 (s, 2H), 6.88 (d, J=9 Hz, 2H), 6.99 (d, J=9 Hz, 2H), 7.12 (d, J=9 Hz,2H), 7.27 (d, J=9 Hz, 2H), 7.65 (m, 4H), 7.78 (m, 2H), 8.00 (m, 4H), 8.40 (t, J=9 Hz, 2H), MS (APCI) m/z 581 (M+H)$^+$. Anal. Calcd for C$_{39}$H$_{36}$N$_2$O$_3$.0.85 H$_2$O: C, 78.59; H, 6.38N, 4.70; Found: C, 78,64; H, 6.41; N, 4.21.

EXAMPLE 4

Preparation of 4,4-bis(4-(2-quinolylmethoxy) phenyl)cyclohexyliminoxyacetic acid sodium salt

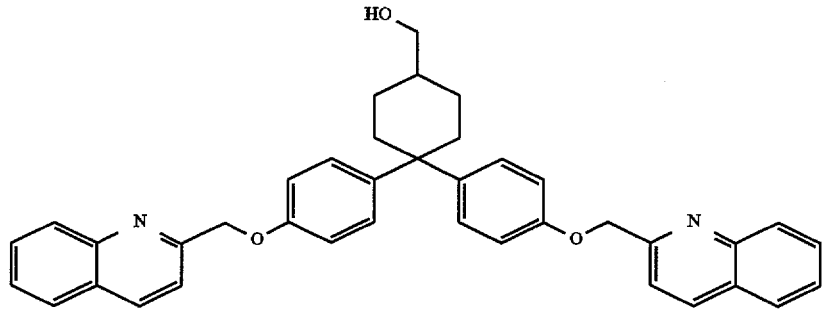

The starting ester (0.60 g, 0.96 mmol) was dissolved in anhydrous THF at room temperature with stirring. Solid lithium aluminum hydride (0.09 g, 2.4 mmol) was added to the solution and the mixture was allowed to stir overnight. The product was worked-up following the standard Fieser &

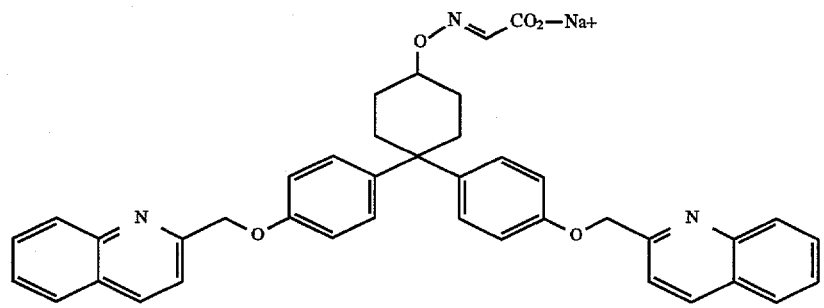

Fieset procedure. The organic layer was dried over Na$_2$SO$_4$,

To a solution of 1,4-cyclohexanedione monoethylene ketal (3.12 g, 20 mmol) in dioxane (25 mL) and ethanol (45 mL) was added NaBH$_4$ (0.38 g, 10 mmol) and the resulting mixture was refluxed for 45 min. The mixture was then cooled to room temperature, acidified to pH 5 with 10% citric acid and extracted with ethyl acetate to afford crude 1-hydroxy-4-cyclohexanone ethylene ketal (2.8 g).

A mixture of ketal intermediate (2.8 g, 17.7 mmol) and phenol (5.64 g, 60 mmol) in dioxane (10 mL) and water (10 mL) at 0° C. was treated dropwise with conc. H$_2$SO$_4$ (20 mL). The mixture was allowed to warm to room temperature and stirred at this temperature for the next 6 h. The reaction mixture was then poured into ice-water and extracted with ethyl acetate. The acetate layer was washed with water, brine, dried with anhydrous MgSO$_4$ and concentrated in vacuo to provide 4,4-bis(4-hydroxyphenyl)cyclohexanol (5 g) contaminated with phenol.

The diphenol derivative was dissolved in DMF (100 mL) and treated with anhydrous K$_2$CO$_3$ (11.04 g, 80 mmol) and 2-chloromethylquinoline hydrochloride (12.84 g, 60 mmol) for 20 h at ambient temperature. The mixture was then diluted with water (500 mL) and extracted with ethyl acetate. The organic layer was washed with water, brine, dried with anhydrous MgSO$_4$ and concentrated in vacuo. The residue was purified by chromatography (silica gel, 4:1 CH$_2$Cl$_2$/EtOAc) to provide 4,4-bis(4-(2-quinolylmethoxy)phenyl)cycohexanol (5.25 g).

To a solution of cyclohexanol intermediate (5.25 g, 9.27 mmol). Ph$_3$P (5.24 g, 20 mmol) and N-hydroxyphthalimide (1.52 g, 9.3 mmol) in THF (5.50 mL) was added dropwise DIAD (4 mL, 20 mmol) in THF (10 mL). The reaction mixture was stirred at ambient temperature for 18 h and then concentrated in vacuo. The residue was chromatographed (silica gel, 15:1 CH$_2$Cl$_2$/EtOAc) to provide N-phthaloyl intermediate (7.1 g).

The phthaloyl intermediate in dioxane (25 mL) and ethanol (25 mL) was refluxed with hydrazine hydrate (1.2 ml, 20 mmol) for 30 min. The mixture was then diluted with 10% sodium carbonate (50 mL) and extracted with ethyl acetate. The organic extract was washed with water, brine, dried with anhydrous MgSO$_4$ and concentrated in vacuo. The residue was purified by chromatography (silica gel, 2:1 CH$_2$Cl$_2$/EtOAc) to provide O-4,4-bis(4-(2-quinolylmethoxy)phenyl)cyclohexylhydroxylamine (0.94 g).

A mixture of hydroxylamine derivative (0.35 g, 0.6 mmol), glyoxylic acid (0.055 g, 0.6 mmol) and acetic acid (0.04 mL, 0.6 mmol) in dioxane (20 mL), methanol (10 mL) and water (5 mL) was stirred at room temperature for 12 h. The organics were then removed under reduced pressure and the residue was diluted with water (30 mL). The pH was adjusted to 3 with 10% citric acid and the solid was filtered and dried under reduced pressure to afford 4,4-bis(4-(2-quinolylmethoxy)phenyl)cyclohexyliminoxyacetic acid (0.37 g, 97%).

To a solution of iminoxyacid in THF (30 mL) was added solid NaOH (0.025 g, 0.64 mmol) followed by water (10 mL) and the resulting mixture was stirred at room temperature for 1 h. The water (20 mL) was added and the THF was removed in vacuo. The water solution was frozen and lyophilized to provide the title compound (0.38 g, 90%): $^1$H NMR (300 MHz, DMSO-d$_6$) δ 1.45 (m, 2H), 1.76 (m, 2H), 2.02 (m, 2H), 2.45 (m, 2H), 4.04 (m, 1H), 5.30 (two s, 4H), 6.91 (d, 2H, J=9 Hz), 6.98 (d, 2H J= 9 Hz), 7.20 (d, 2H, J=9 Hz), 7.27 (d, 2H, J=9 Hz), 7.62 (m, 4H), 7.78 (m, 1H), 8.00 (m, 4H), 8.40 (two d, 2H, J=8 Hz); MS (FAB(+)) m/z 638 (M+H)$^+$, 660 (M+Na)$^+$; MS (FAB(−)) m/z 636 (M−H)−.Anal. Calcd for C$_{40}$H$_{34}$N$_3$O$_5$Na: C, 72.82; H, 5.19; N, 6.36; Found: C, 72.51; H, 5.35; N, 6.71.

EXAMPLE 5

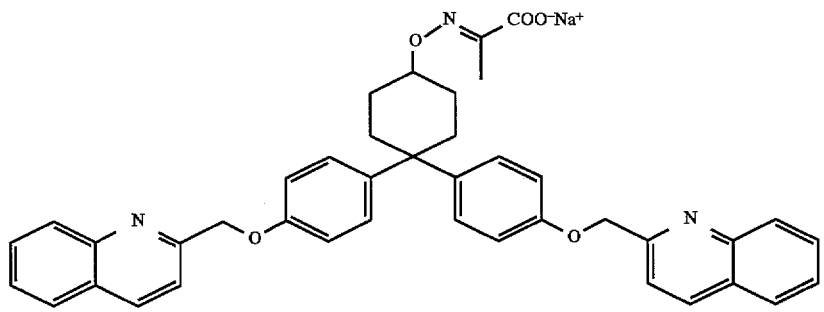

Preparation of 4,4-bis(4-(2-quinoloylmethoxy)phenyl)cyclohexyliminoxy-2-propionic acid sodium salt The solution of O-4,4-bis(4-(2-quinolylmethoxy)phenyl)cyclohexylhydroxylamine resulting from Example 4 (0.58 g, 1 mmol) and methyl pyruvate (0.1 mL, 1 mmol) in dioxane (20 mL) and methanol (10 mL) was treated with acetic acid (0.06 mL, 1 mmol) at room temperature for 10 h. The mixture was concentrated in vacuo, dissolved in ethyl acetate and washed with saturated NaHCO$_3$, brine, dried with anhydrous MgSO$_4$ and concentrated in vacuo. The residue was chromatographed (silica gel, 4:1 CH$_2$Cl$_2$/EtOAc) to provide 4,4-bis(4-(2-quinolylmethoxy)phenyl)cyclohexyliminoxy-2-propionic acid methyl ester (0.54 g).

To a solution of iminoxyester from above in dioxane (15 mL) and methanol (10 mL) was added 1N NaOH (1 mL) and the reaction mixture was stirred at room temperature for 10 h. The organics were removed in vacuo, the residue was diluted with water (25 mL) and acidified to pH 3 with 10% citric acid. The solid was filtered and dried in vacuo. The crude acid was redissolved in THF, filtered and concentrated in vacuo to get 4,4-bis(4-(2-quinolylmethoxy)phenyl)cyclohexyliminoxy-2-propionic acid (0.52 g).

A powder NaOH (0.032 g, 0.8 mmol) was added to a solution of iminoxyacid intermediate (0.52 g, 0.8 mmol) in THF (50 mL) followed by addition of water (10 mL) and the mixture was stirred at room temperature for 30 min. The water (15 mL) was added and the THF was removed in vacuo. The water solution was frozen and lyophilized to get the title compound: mp 107°–113° C.; $^1$H NMR (300 MHz, DMSO-d$_6$) δ 1.47 (m, 2H), 1.73 (m+s, 5H), 2.05 (m, 2H), 2.44 (m, 2H), 4.07 (m, 1H), 5.30 (two s, 4H), 693 (d, 2H, J=9

Hz), 6.98 (d, 2H, J=9 Hz), 7.21 (d, 2H, J=9 Hz), 7.26 (d, 2H, J=9 Hz), 7.63 (m, 4H), 7.78 (m, 2H), 8.00 (m, 4H), 8.40 (two d, 2H, J=8 Hz); MS (FAB(+)) m/z 652 (M+H)⁺, 674 (M+Na)⁺; MS (FAB(−)) m/z 650 (M−H)−.Anal. Calcd for $C_{41}H_{36}N_3O_5Na \times 2H_2O$: C, 69.38; H, 5.68; N, 5.92; Found: C, 69.27; H, 5.63; N, 5.83.

EXAMPLE 6

Preparation of 4,4-bis(4-(2-quinolylmethoxy) phenyl)-1-cyclohexylmethyliminoxyacetic acid

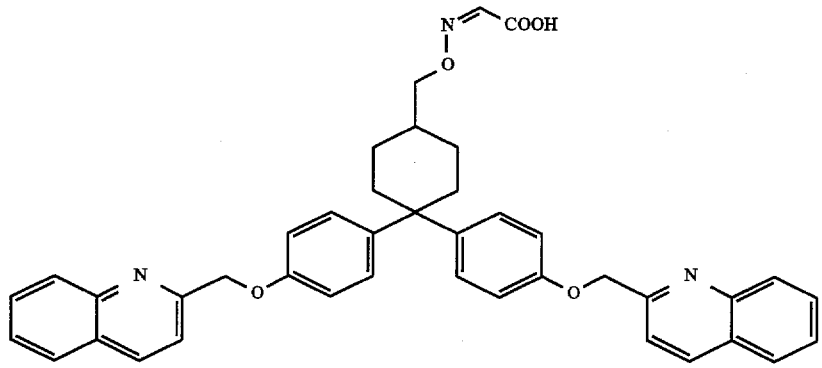

The desired material was prepared according to the procedure of Example 4 except substituting 4,4-bis(4-(2-quinolylmethoxy)phenyl)-1-cyclohexylmethanol, resulting from Example 3, for 4,4-bis(4-(2-quinolylmethoxy)phenyl)-1-cyclohexanol mp 91°–97° C.; $^1$H NMR (300MHz, DMSO-$d_6$) δ 1.10 (m, 2H), 1.66 (m, 2H), 1.81 (m, 3H), 2.67 (m, 2H), 3.99 (d, J=7.5 Hz, 2H), 5.28 (s, 2H), 5.32 (s, 2H), 6.88 (d, J=9 Hz, 2H), 7.00 (d, J=9 Hz, 2H), 7.11 (d, J=9 Hz, 2H), 7.28 (d, J=9 Hz, 2H), 7.51 (s, 1H), 7.62 (m, 3H), 7.68 (d, J=9 Hz, 1H), 7.78 (m, 2H), 8.00 (m, 4H), 8.40 (t, J=9 Hz, 2H); MS (APCI) m/z 652 (M+H)⁺. Anal. Calcd for $C_{41}H_{37}N_3O_5 \cdot 0.50\ H_2O$: C, 74.52; H, 5.79; N, 6.35; Found: C, 74.60; H, 5.91; N, 5.89.

EXAMPLE 7

Preparation of 4,4-bis(4-(2-quinolylmethoxy) phenyl)-1-cyclohexyloximinoacetic acid

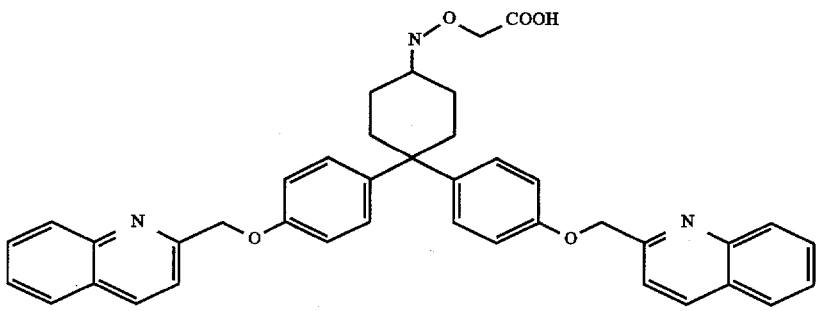

To a mixture of 4,4-bis(4-(2-quinolylmethoxy)phenyl) cyclohexanol (resulting from Example 4) (1.13 g, 2 mmol) and molecular sieves (3 g) in $CH_2Cl_2$ (40 mL) was added PCC (0.65 g, 3 mmol) and the resulting mixture was stirred at room temperature for 30 min. The mixture was filtered through the Celite, the filtrate was concentrated in vacuo to 10 mL and then chromatographed (silica gel, 4:1 $CH_2Cl_2$/EtOAc) to afford 0.25 g of 4,4-bis(4-(2-quinolylmethoxy) phenyl)cyclohexanone.

A mixture of ketone from above (0.25 g, 0.44 mmol), $H_2NOH \times HCl$ (0.035 g, 0.5 mmol) and $AcONa \times 3H_2O$ (0.68 g, 0.5 mmol) in dioxane (15 mL), MeOH (10 mL) and $H_2O$ (8 mL) was stirred at room temperature for 18 h and then concentrated in vacuo. To the residue was added water (30 mL), the solid was filtered and dried in vacuo to provide 0.22 g of 4,4-bis(4-(2-quinolylmethoxy)phenyl)cyclohexanone oxime.

The solution of oxime (0.022 g, 0.38 mmol) in DMF (20 mL) was treated with ethyl bromoacetate (0.06 mL, 0.5 mmol) in the presence of $Cs_2CO_3$ (0.17 g, 0.5 mmol) for 48 h at room temperature. The mixture was then diluted with water and extracted with ethyl acetate. The acetate layer was washed with water, brine, dried with $MgSO_4$ and concentrated in vacuo. The residue was chromatographed (silica gel, 2:1 $CH_2Cl_2$/EtOAc) to give 0.125 g of 4,4-bis(4-(2-quinolylmethoxy)phenyl)cyclohexyloximinoacetic acid ethyl ester.

A solution of 1N NaOH (0.3 mL, 0.3 mmol) was added to ester (0.125 g, 0.19 mmol) in dioxane (10 mL) and EtOH (6 mL) and the reaction was continued at room temperature for the next 6 h. The organics were removed in vacuo, the residue was diluted with water and acidified to pH 3 with 10% citric acid. The solid was filtered, dried in vacuo and crystallized from dioxane-water to provide 0. 11 g (90%) of the title compound: mp 109°–111° C.; $^1$H NMR (300 MHz, DMSO-$d_6$) δ 2.14 (m, 2H), 2.33 (m, 4H), 2.45 (m, 2H), 4.43 (s, 2H), 5.30 (s, 4H), 6.97 (d, J=9 Hz, 4H), 7.25 (d, J=9 Hz, 4H), 7.63 (m, 4H), 7.78 (m, 2H), 8.00 (m, 4H), 8.40 (d, J=8 Hz, 2H); MS (APCI+QIMS LMR UP LR) m/z 638 (M+H)⁺. Anal. Calcd for $C_{40}H_{35}N_3O_5 \times 0.75\ H_2O$: C, 73.77; H, 5.64; N, 6.45. Found: C, 73.77; H, 5.54; N, 6.17.

EXAMPLE 8

Preparation of 4,4-bis-(4-(2-benzothiazolylmethoxy) phenyl)cyclohexane carboxylic acid

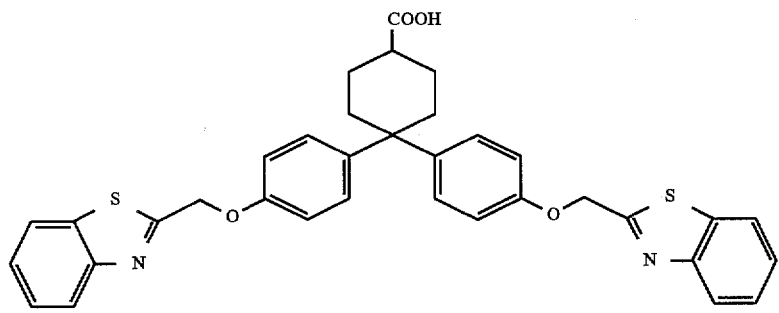

The method of Example 1 is used with substitution of 2-chloromethylbenzothiazole for 2-chloromethylquinoline.

EXAMPLE 9

Preparation of 4,4-bis-(4-(2-quinoxalylmethoxy) phenyl)cyclohexane carboxylic acid

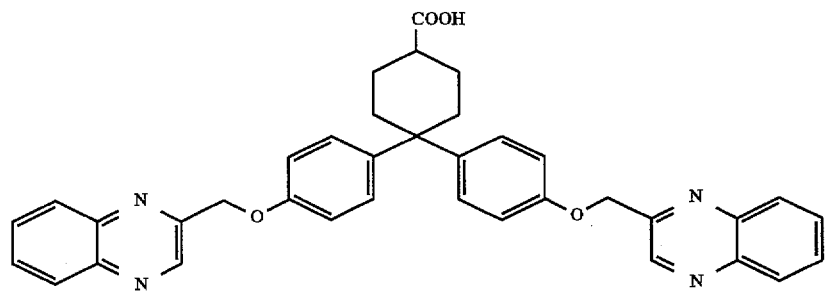

The method of Example 1 is used with substitution of 2-chloromethylquinoxaline for 2-chloromethylquinoline.

EXAMPLE 10

Preparation of 4,4-bis-(4-(7-chloro-2-quinolylmethoxy)phenyl)cyclohexane carboxylic acid

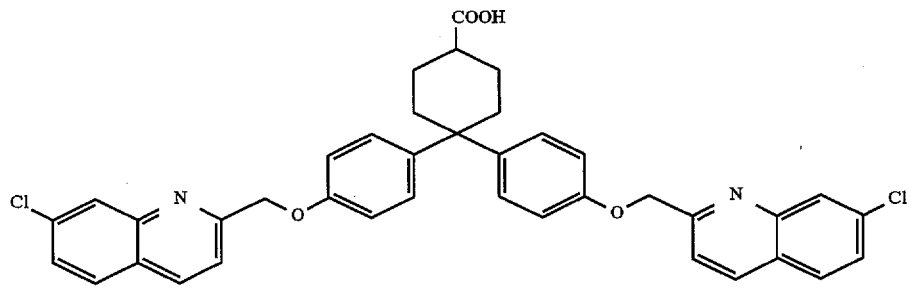

The method of Example 1 is used with substitution of 7-chloro-2-chloromethylquinoline for 2-chloromethylquinoline.

EXAMPLE 11

Preparation of 4,4-bis-(4-(2-benzothiazolylmethoxy)phenyl)cyclohexylmethanol

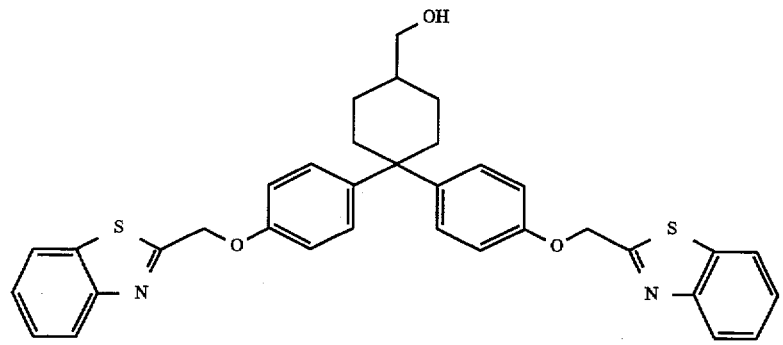

The method of Example 3 is used with the product of Example 8.

EXAMPLE 12

Preparation of 4,4-bis-4-2-quinoxalylmethoxy)phenyl)cyclohexylmethanol

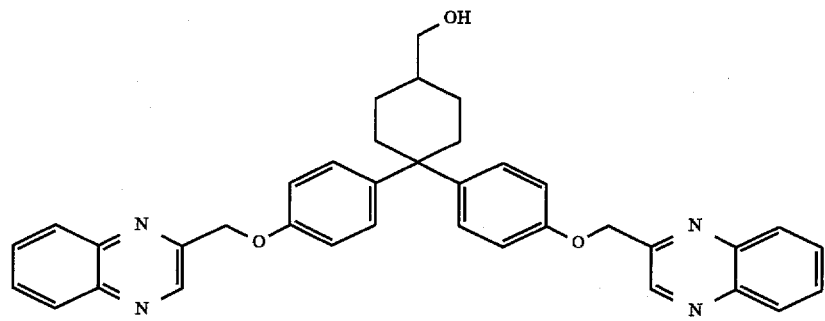

The method of Example 3 is used with the product of Example 9.

EXAMPLE 13

Preparation of 4 4-bis-(4-(7-chloro-2-quinolylmethoxy)phenyl)cyclohexylmethanol

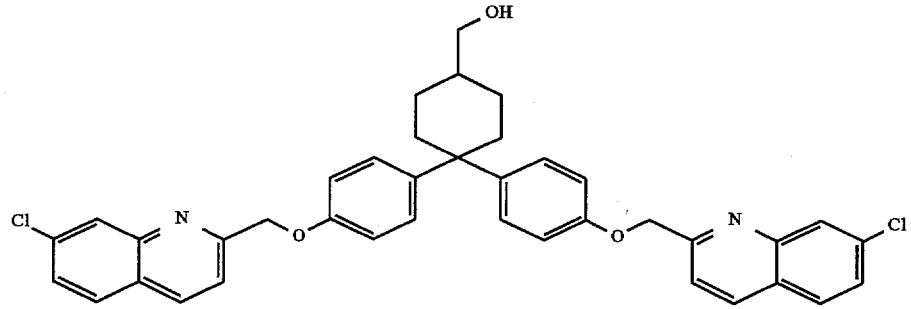

The method of Example 3 is used with the product of Example 10.

EXAMPLE 14

Preparation of 4,4-bis-(4(2-benzothiozolylmethoxy)phenyl)cyclohexylmethyliminoxy acetic acid

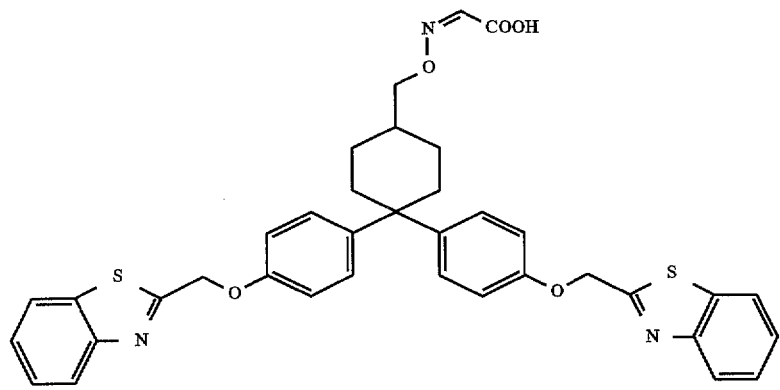

The method of Example 6 is used with the product of Example 11.

EXAMPLE 15

Preparation of 4,4-bis-(4-(2-quinoxalylmethoxy)phenyl)cyclohexylmethyliminoxy acetic acid

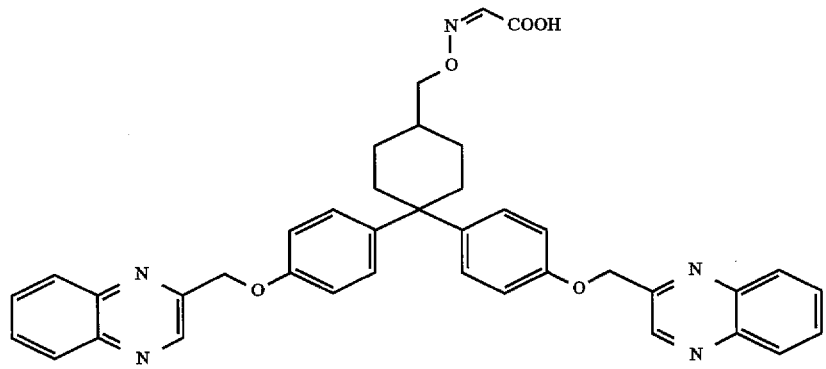

The method of Example 6 is used with the product of Example 12.

EXAMPLE 16

Preparation of 4,4-bis-(4-(7-chloro-2-quinolylmethoxy)phenyl)cyclohexylmethyliminoxy acetic acid

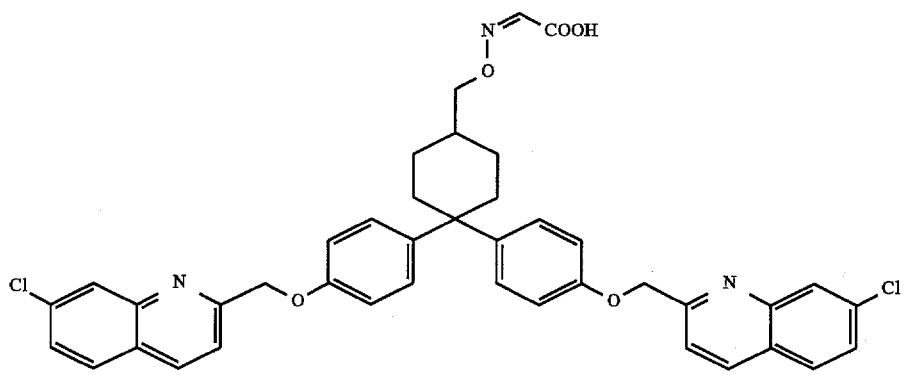

The method of Example 6 is used with the product of Example 13.

EXAMPLE 17

Preparation of 4,4-bis(4-(2-benzothiazolylmethoxy)phenyl)cyclohexyliminoxy-2-propionic acid sodium salt

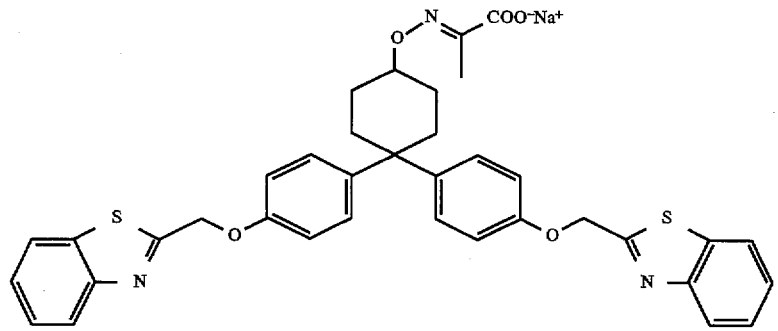

The method of Example 5 is used with substitution of 2-chloromethylbenzothiazole for 2-chloromethylquinoline.

EXAMPLE 18

Preparation of 4,4-bis-(4-(2-quinoxalylmethoxy)phenyl)cyclohexyliminoxy-2-propionic acid sodium salt

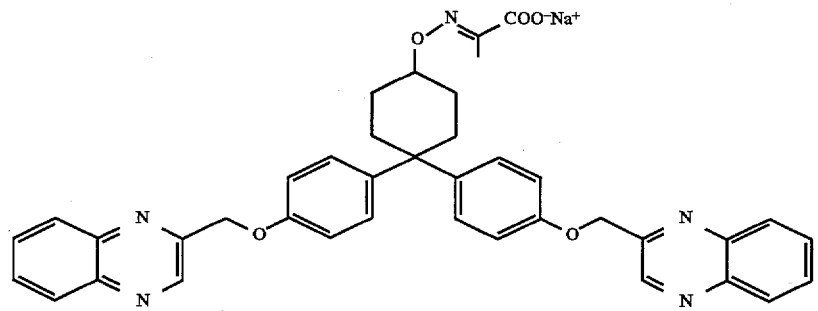

The method of Example 5 is used with substitution of 2-chloromethylquinoxaline for 2-chloromethylquinoline.

EXAMPLE 19

Preparation of 4,4-bis-(4-(7-chloro-2-quinolylmethoxy)phenyl)cyclohexyliminoxy-2-propionic acid sodium salt

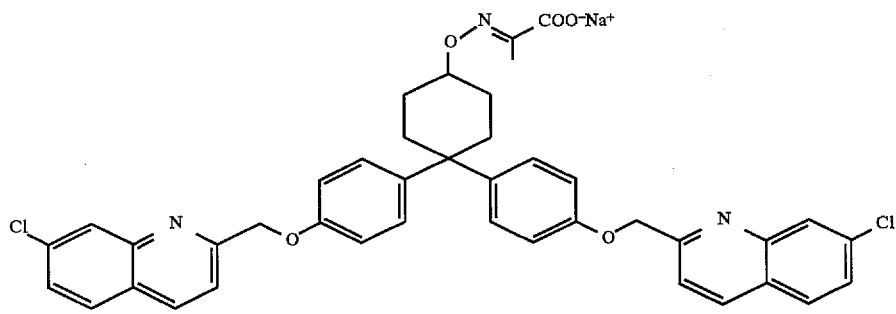

The method of Example 5 is used with substitution of 7-chloro-2-chloromethylquinoline for 2-chloromethylquinoline.

EXAMPLE 20

Preparation of 4,4-bis-(4-(2-benzothiazolylmethoxy)phenyl)cyclohexyliminoxyacetic acid sodium salt

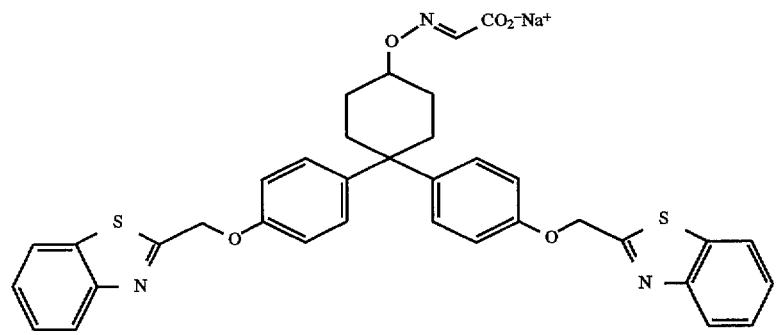

The method of Example 4 is used with substitution of 2-chloromethylbenzothiazole for 2-chloromethylquinoline.

EXAMPLE 21

Preparation of 4,4-bis-(4-(2-quinoxalylmethoxy)phenyl)cyclohexyliminoxyacetic acid sodium salt

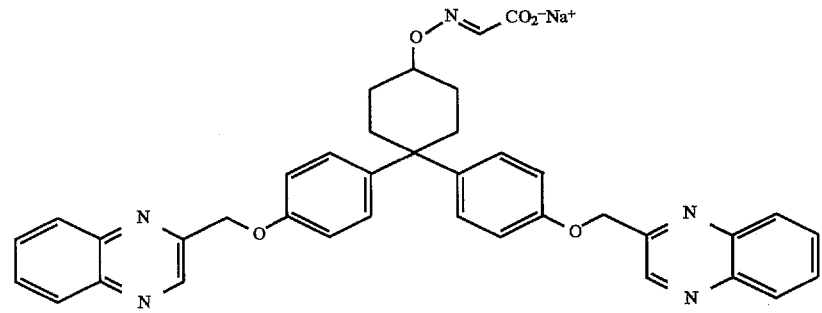

The method of Example 4 is used with substitution of 2-chloromethylquinoxaline for 2-chloromethylquinoline.

EXAMPLE 22

Preparation of 4,4-bis-(4-(7-chloro-2-quinolylmethoxy)phenyl)cyclohexyliminoxyacetic acid sodium salt

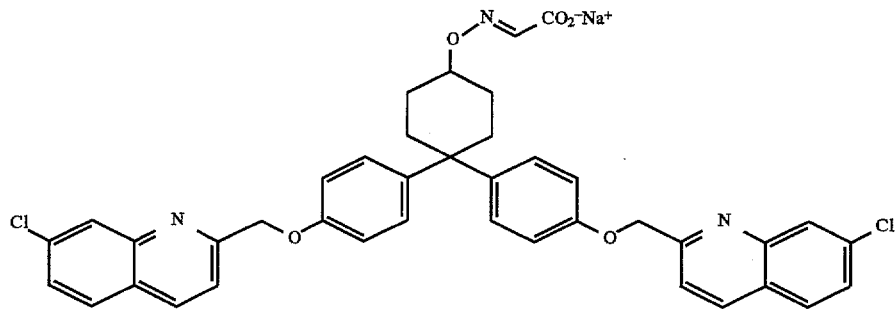

The method of Example 4 is used with substitution of 7-chloro-2-chloromethylquinoline for 2-chloromethylquinoline.

EXAMPLE 23

Preparation of 4,4-bis-(4-(2-benzothiazolylmethoxy)phenyl)cyclohexyloximinoaeetic acid

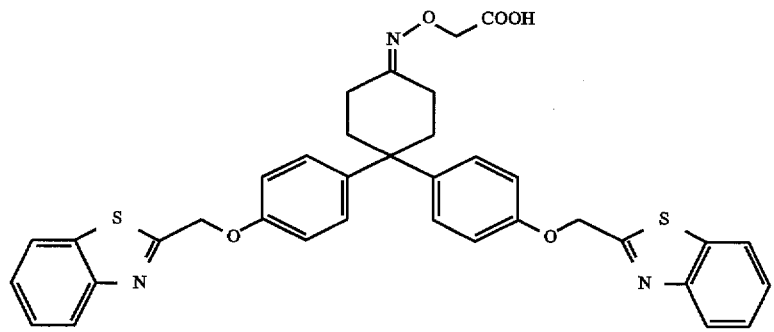

The method of Example 7 is used with the cyclohexanol intermediate from Example 20.

EXAMPLE 24

Preparation of 4,4-bis-(4(2-quinoxalylmethoxy)phenyl)cyclohexyloximinoacetic acid

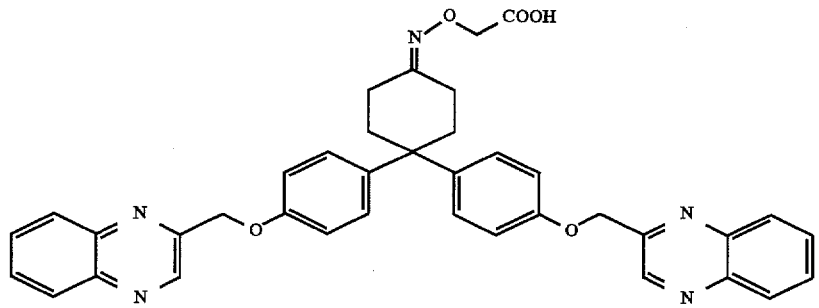

The method of Example 7 is used with the cyclohexanol intermediate from Example 21.

EXAMPLE 25

Preparation of 4,4-bis-(4-(7-chloro-2-quinolylmethoxy)phenyl)cyclohexyloximinoacetic acid

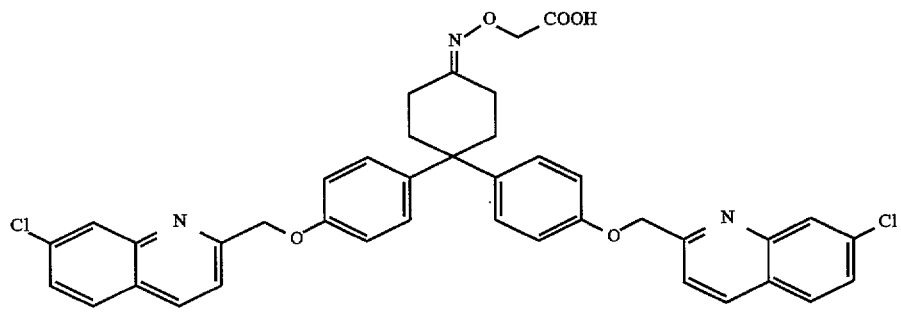

The method of Example 7 is used with the cyclohexanol intermediate from Example 22.

The method of Example 1 is used with substitution of methyl 3-oxocyclobutane-1-carboxylate (Bashir-Hashemi, A.; Hardee, J. R. *J. Org. Chem.* 1994, 59, 2132–2134) for ethyl 4-oxocyclohexanecarboxylate.

EXAMPLE 26

Preparation of 5,5-bis-(4-(2-quinolylmethoxy)phenyl)cyclooctanecarboxylic acid

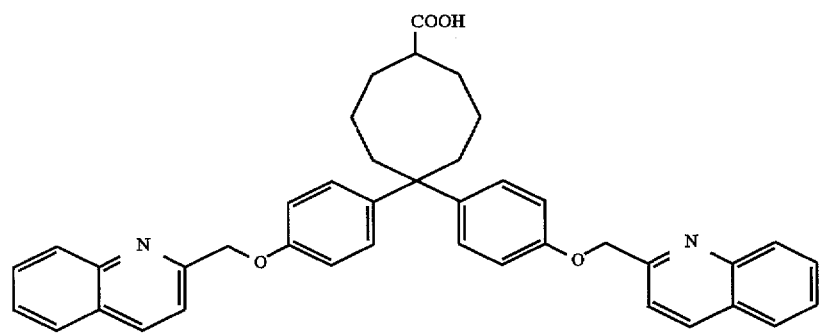

The method of Example 1 is used with substitution of 5-oxocyclooctane-1-carboxylic acid (Curran, D. P.; Shen, W. Tandem *Tetrahedron* 1993, 49, 755–770) for ethyl 4-oxocyclohexanecarboxylate.

EXAMPLE 27

Preparation of 3,3-bis-(4-(2-quinolylmethoxy)phenyl)cyclobutanecarboxylic acid

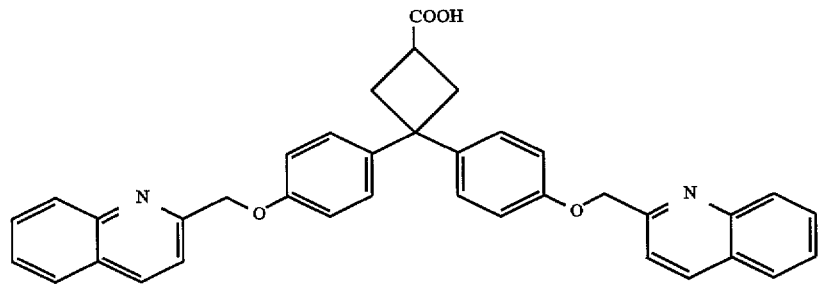

EXAMPLE 28

Preparation of 3,3-bis-(4-(2-quinolylmethoxy) phenyl)cyclopentanecarboxylic acid

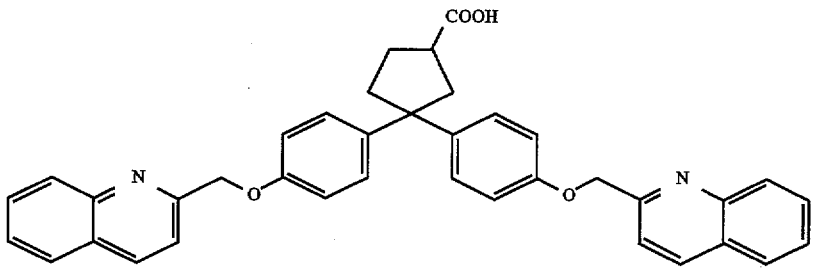

The method of Example 1 is used with substitution of methyl 3-oxocyclopentyl-1-carboxylate (Bashir-Hashemi, A.; Hardee, J. R. *J. Org. Chem.* 1994, 59, 2132–2134) for ethyl 4-oxocyclohexanecarboxylate.

EXAMPLE 29

Preparation of 3,3-bis-(4-(2-quinolylmethoxy) phenyl)cyclohexanecarboxylic acid

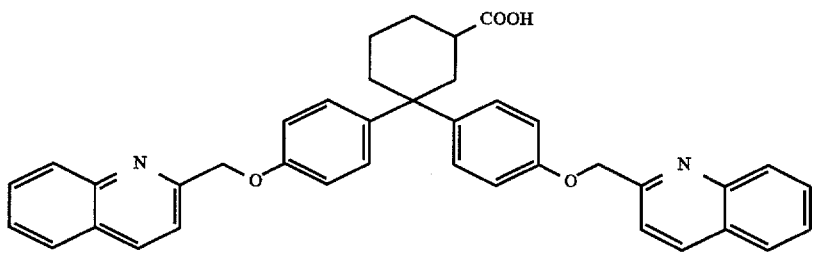

The method of Example 1 is used with substitution of methyl 3-oxocyclohexyl-1-carboxylate (Dowd, P.; Choi, S. C. *Tetrahedron* 1989, 45, 77–90) for ethyl 4-oxocyclohexanecarboxylate.

EXAMPLE 30

Preparation of 3,3-bis-(4-(2-quinolylmethoxy) phenyl)cycloheptanecarboxylic acid

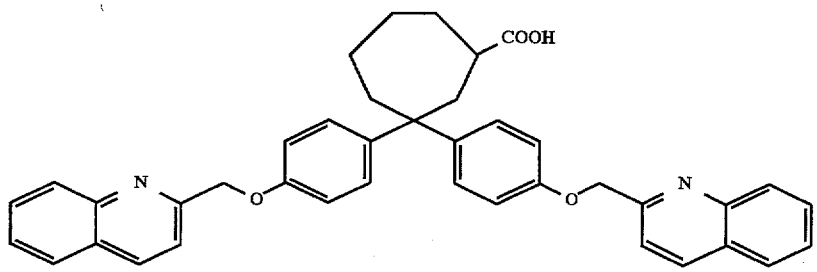

The method of Example 1 is used with substitution of methyl 3-oxocycloheptyl-1-carboxylate (Dowd, P.; Choi, S. C. *Tetrahedron* 1989, 45, 77–90) for ethyl 4-oxocyclohexanecarboxylate.

EXAMPLE 31

Preparation of 3,3-bis-(4-(2-quinolylmethoxy) phenyl)cyclooctanecarboxylic acid

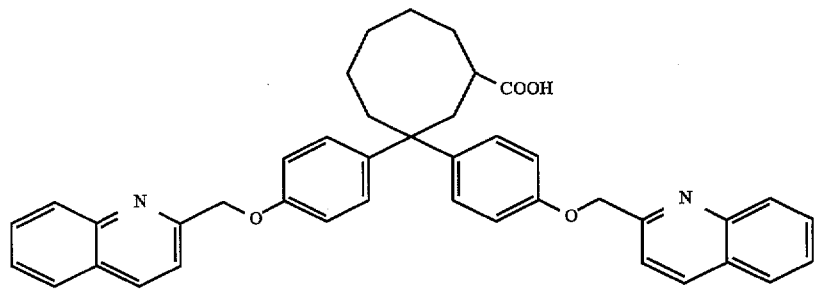

The method of Example 1 is used with substitution of methyl 3-oxocycloctyl-1-carboxylate (Dowd, P.; Choi, S. C. *Tetrahedron* 1989, 45, 77–90) for ethyl 4-oxocyclohexanecarboxylate.

EXAMPLE 32

Preparation of 3,3-bis-(4-(2-quinolylmethoxy) phenyl)cyclobutyliminoxyacetic acid sodium salt

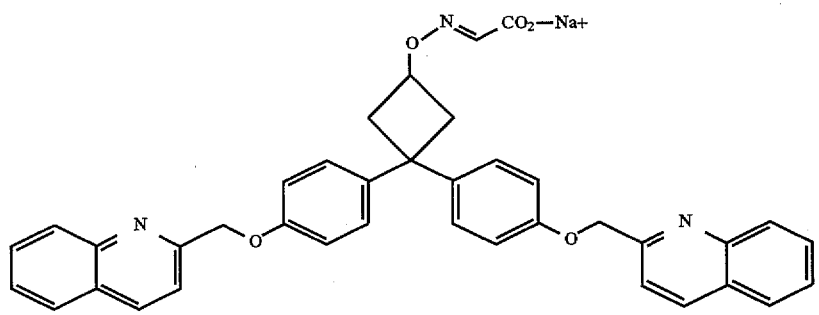

The method of Example 4 is used with substitution of 3-oxocyclobutanone (Tenud, L.; Weilenmann, M.; Dallwigk, E. *HelveticalChimica Acta* 1977, 60, 975–977) for 1-hydroxy-4-cyclohexanone ethylene ketal.

EXAMPLE 33

Preparation of 3,3-bis-(4-(2-quinolylmethoxy) phenyl)cyclopentyliminoxyacetic acid sodium salt

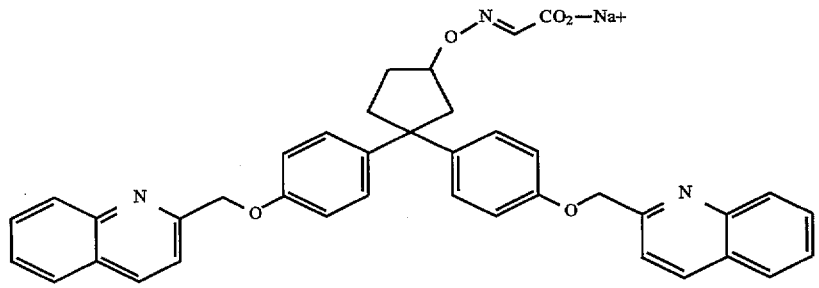

The method of Example 4 is used with substitution of 3-oxocyclopentanone (Mcintosh, J. M.; Beaumier, P. *J. Org. Chem.* 1938, 57, 2905–2906) for 1-hydroxy-4-cyclohexanone ethylene ketal.

EXAMPLE 34

Preparation of 3,3-bis-(4-(2-quinolylmethoxy)phenyl)cyclooctylliminoxyacetic acid sodium salt The method of Example 4 is used with substitution of 3-oxocyclooctanone (Cope, A. C.; Fiaher, B. S.; Funke, W.; Mcintosh, J. M.; McKervey, M. A. *J. Org. Chem.* 1969, 34, 2231-2234) for 1-hydroxy-4-cyclohexanone ethylene ketal.

We claim:

1. A compound having the structural formula I:

or a pharmaceutically acceptable salt thereof wherein
m is an integer of 1 to 9, inclusive;
n is an integer of 1 to 4, inclusive;
W is the same at each occurrence and is selected from the group consisting of
 (a) unsubstituted quinolyl;
 (b) quinolyl substituted with one, two, or three substituents selected from the group consisting of
  halogen,
  $C_{1-6}$ alkyl, and
  $C_{1-6}$ alkoxy;
 (c) unsubstituted benzothiazoyl;
 (d) benzothiazoyl substituted with one, two, or three substituents selected from the group consisting of
  halogen,
  $C_{1-6}$ alkyl, and
  $C_{1-6}$ alkoxy;
 (e) unsubstituted quinoxalyl; and
 (f) quinoxalyl substituted with one, two, or three substituents selected from the group consisting of
  halogen,
  $C_{1-6}$ alkyl, and
  $C_{1-6}$ alkoxy;
Y is one to four substituents independently selected from
 halogen,
 $C_{1-6}$ alkyl, and
 $C_{1-6}$ alkoxy;
X is absent or is selected from the group consisting of
 (a) $C_{1-6}$ alkylene;
 (b) $C_{1-6}$ alkenylene; and
 (c) $C_{1-6}$ alkynylene;
Z is selected from the group consisting of
 (a) COB;
 (b) $C(R^2)_2$—O—N=A—COB; and
 (c) $C(R^2)$=N—O—A—COB where
  A is $C_{1-6}$ alkylene, and
  B is selected from the group consisting of
   (a) —OH,
   (b) —O⁻M⁺ where M is a pharmaceutically acceptable cation;
   (c) —OR⁶ where R⁶ is hydrogen or alkyl of one to six carbon atoms;
   (d) —NR⁶R⁷ where R⁶ is as previously defined and R⁷ is selected from the group consisting of
    hydrogen,
    alkyl of one to six carbon atoms,
    hydroxy, and
    alkoxy or from one to six carbon atoms, or
    R⁶ and R⁷, together with the atom to which they are attached, form a ring of five to eight members containing one optional heteratom selected from N, and S; and
   (e) —O—D where D is a metabolically cleavable group.

2. A compound as defined by claim 1 or pharmaceutically acceptable salt thereof wherein W is selected from the group consisting of
 unsubstituted quinolyl, and
 quinolyl substituted with one, two, or three substituents selected from the group consisting of
  halogen,
  $C_{1-6}$ alkyl, and
  $C_{1-6}$ alkoxy.

3. A compound as defined by claim 1 or pharmaceutically acceptable salt thereof wherein W is selected from the group consisting of
 unsubstituted benzothiazolyl, and
 benzothiazolyl substituted with one, two, or three substituents selected from the group consisting of
  halogen,
  $C_{1-6}$ alkyl, and
  $C_{1-6}$ alkoxy.

4. A compound as defined by claim 1 or pharmaceutically acceptable salt thereof wherein W is selected from the group consisting of
 unsubstituted quinoxalyl, and
 quinoxalyl substituted with one, two, or three substituents selected from the group consisting of
  halogen,
  $C_{1-6}$ alkyl, and
  $C_{1-6}$ alkoxy.

5. A compound as defined by claim 1 or a pharmaceutically acceptable salt thereof wherein m is an integer of one to three, inclusive.

6. A compound as defined by claim 2 thereof selected from the group consisting of 4,4-bis-(4-(2-quinolylmethoxy)phenyl)cyclohexane carboxylic acid;

4,4-bis-(4-(2-quinolylmethoxy)phenyl)cyclohexane carboxylic acid sodium salt:

4,4-bis-(4-(2-quinolylmethoxy)phenyl) cyclohexyliminoxyacetic acid sodium salt;

4,4-bis-(4-(2-quinolylmethoxy)phenyl)cyclohexyliminoxy-2-propionic acid sodium salt;

4,4-bis-(4-(2-quinolylmethoxy)phenyl)-1-cyclohexylmethyliminoxyacetic acid; and 4,4-bis-(4-(2-quinolylmethoxy)phenyl)-1-cyclohexyloximinoacetic acid.

7. A pharmaceutical formulation comprising a leukotriene biosynthesis inhibitory effective amount of a compound as defined by claim 1 in combination with a pharmacutically acceptable carrier.

8. A method of inhibiting leukotriene biosynthesis in a mammal in need of such treatment comprising administering to said mammal a leukotriene biosynthesis inhibitory effective amount of a compound as defined by claim 1.

* * * * *